(12) United States Patent
Witt

(10) Patent No.: US 9,309,173 B2
(45) Date of Patent: Apr. 12, 2016

(54) PROCESS STREAM DECONTAMINATION SYSTEMS AND METHODS

(71) Applicant: Lance Witt, Sugar Land, TX (US)

(72) Inventor: Lance Witt, Sugar Land, TX (US)

( * ) Notice: Subject to any disclaimer, the term of this patent is extended or adjusted under 35 U.S.C. 154(b) by 0 days.

(21) Appl. No.: 14/503,730

(22) Filed: Oct. 1, 2014

(65) Prior Publication Data

US 2015/0037208 A1  Feb. 5, 2015

Related U.S. Application Data

(63) Continuation of application No. 13/833,023, filed on Mar. 15, 2013, now Pat. No. 8,877,126.

(51) Int. Cl.

| *A61L 9/00* | (2006.01) |
|---|---|
| *G05B 1/00* | (2006.01) |
| *G01D 11/26* | (2006.01) |
| *C07C 7/20* | (2006.01) |
| *B01J 19/00* | (2006.01) |
| *B01D 12/00* | (2006.01) |
| *C02F 1/00* | (2006.01) |
| *C10G 29/00* | (2006.01) |
| *B01J 19/08* | (2006.01) |
| *B01J 19/10* | (2006.01) |
| *C10G 21/00* | (2006.01) |
| *C02F 1/04* | (2006.01) |

(52) U.S. Cl.
CPC . *C07C 7/20* (2013.01); *B01D 12/00* (2013.01); *B01J 19/0006* (2013.01); *B01J 19/087* (2013.01); *B01J 19/10* (2013.01); *C02F 1/00* (2013.01); *C10G 21/00* (2013.01); *C10G 29/00* (2013.01); *B01J 2219/182* (2013.01); *C02F 1/04* (2013.01)

(58) Field of Classification Search
CPC ............. A61L 9/00; A61L 9/015; A61L 9/03; A61L 2/00; A61L 2/22; B05B 1/28
USPC .............. 422/3, 5, 28, 32, 105, 119, 305–306
See application file for complete search history.

(56) References Cited

U.S. PATENT DOCUMENTS

2004/0120845 A1*  6/2004  Potember ................ A61L 9/015
422/4

\* cited by examiner

*Primary Examiner* — Monzer R Chorbaji
(74) *Attorney, Agent, or Firm* — Shawn Hunter

(57) ABSTRACT

A decontamination system for decontaminating at least one contaminant in a process stream. Decontaminant liquid is dispersed into the process stream using atomization. A controller detects contaminant levels in the process stream and adjusts the flow of decontaminant fluid into the process stream in response.

19 Claims, 5 Drawing Sheets

PROCESS STREAM DECONTAMINATION SYSTEMS AND METHODS

BACKGROUND OF THE INVENTION

1. Field of the Invention

The invention relates generally to systems and methods used to decontaminate process streams that contain at least one contaminant. In particular aspects, the invention relates to systems and methods for decontaminating natural gas, liquid petroleum products or water in pipelines or production streams and for monitoring and control of the decontamination process.

2. Background of the Invention

Regulations require companies that produce or supply natural gas, crude oil, liquid petroleum gas or water to monitor product contaminants, mitigate potential hazards and maintain quality specifications. Typical contaminants include hydrogen sulfide ($H_2S$), carbon dioxide ($CO_2$), oxygen ($O_2$), and biological populations. These contaminants can cause pipeline corrosion and subsequent rupture, narrowing of the line due to deposits, plugging, precipitation of solids, etc. Hydrogen sulfide, for example, is a highly corrosive and deadly substance that occurs naturally in a large number of hydrocarbon formations in south Texas and around the world. Hydrogen sulfide is not only harmful to humans, but when left untreated, can quickly corrode pipelines, potentially leading to ruptures and explosions. The U.S. Department of Transportation mandates that certain pipelines contain no more than 4 ppm of hydrogen sulfide at any given time. This is an extremely low concentration and can be difficult to measure accurately.

Conventional methods for treatment of contaminants have drawbacks. Depending upon the nature of the contaminant, a chemical scavenger or curative is typically added to the process stream. Inaccuracies in measurement of the contaminant frequently lead to overuse of injected curative. Operators routinely overcompensate when attempting to mitigate a risk by injecting excess chemical into the process stream. Because chemicals can be expensive, overuse translates into significant financial waste. Additionally, high levels of excess chemical can accumulate and must be removed or can build up on the pipeline wall, creating a rock-hard scale. Under certain conditions, rock hard scale builds up and can restrict the flow of gas causing further negative effects. If too much scale accumulates, the pipeline will require treatment with other potentially hazardous and expensive chemicals resulting in further health and safety risks and monetary loss.

SUMMARY OF THE INVENTION

The present invention provides systems and methods for monitoring selected contaminants in a process stream and, in response, providing a selected amount of an appropriate decontaminant to neutralize the contaminant. In particular embodiments, the process stream can be natural gas flowing through a pipeline. In other embodiments, the process stream can be a flow of other liquids, such as crude oil or water. Typical contaminants include hydrogen sulfide ($H_2S$), mercaptans, carbon dioxide ($CO_2$), oxygen ($O_2$), water ($H_2O$) and biological populations. In addition, a detected "contaminant," as discussed herein, can include conditions that can lead to contaminants, such as conditions that are ideal for hydrate formation and corrosion.

In one aspect, the invention includes an automated controller and a chemical analyzer that is operably associated with one or more detectors that measure the amount or concentration(s) of one or more contaminants within the process stream. Preferably, the controller is also operably associated with multiple sensors that measure decontaminant levels, flow rates, pressures, volumes, power, analyzer functions, maintenance requirements, etc. In addition, the controller is operably associated with one or more supplies of decontaminant that is/are injected into the process stream to neutralize the contaminant or contaminants. The decontaminant(s) is/are selected to cure, scavenge or otherwise remove or treat a selected contaminant or prevent a destructive condition.

According to particular aspects, a decontamination system in accordance with the present invention introduces one or more selected decontaminants into the process stream by reducing a liquid containing the decontaminant to a spray of fine droplets (i.e., atomizing the liquid). In a described embodiment, the atomized decontaminant-containing liquid is introduced into the process stream when the process stream is in a gaseous state. The inventor has found that the use of an atomizing spray to introduce a decontaminant is highly effective and optimizes the contact time and amount of exposure which the process stream has to the decontaminant. In preferred embodiments, the atomizing spray has droplets that are no larger than 50 microns in diameter.

An exemplary chemical treatment system is described which includes an in-line vaporization vessel within which atomization occurs. In a described embodiment, a liquid atomization assembly is used in which atomizing nozzles disperse decontaminant liquid into the process stream while the process stream is in a gaseous state.

In particular embodiments, the conduit between the pump and atomizing assembly includes a pulsation dampener that helps ensure that consistent atomization occurs. An exemplary pulsation dampener is a pressure loaded accumulator having a flexible bladder that is pre-loaded with an inert gas of a prescribed pressure. The relaxed bladder is compressed until the inert gas pre-charge can no longer compress. During the back stroke cycle of the chemical pump, when there is no pressure on the atomizer, the pulsation dampener bladder will become a secondary pump as the bladder applies pressure to the liquid stream, thus maintaining the fine atomization desired.

In described embodiments, decontamination systems in accordance with the present invention include a recirculation mechanism. The recirculation mechanism allows for decontaminant to be reused in the system, thereby preventing waste and reducing the amount of spent decontaminant that must be transported and disposed of. In a described embodiment, the recirculation system mechanism includes a means for collecting used decontamination liquid, a chemical sensor, a recirculation pump and recirculation tank for temporary storage of recirculated liquid. The chemical sensor monitors the decontaminant to determine the extent of usability relative to fresh decontaminant. As the decontaminant reacts with the contaminant, the usability decreases. The unusable portion is said to be spent or saturated. The chemical sensor determines if reinjection is possible or, alternatively, if dumping to the waste tank is required.

In operation, decontamination systems in accordance with the present invention operate to monitor and control treatment to remove or neutralize selected contaminants from a process stream such as a pipeline or production stream of natural gas. According to an exemplary method of operation, a quantity of natural gas within a pipeline or production stream is flowed into an in-line vaporization vessel. One or more contaminant analyzers then detect the presence of a pre-selected contaminant as the gas enters and exits the vaporization vessel. The chemical analyzers qualify and quantify the contaminant and provide real time data to the controller. If an excessive amount of a preselected contaminant is detected by the analyzers, the controller will cause the pump(s) to inject/flow an amount of decontaminant liquid into the vaporization vessel. The decontaminant is atomized into the natural gas as the decontaminant enters the vessel.

A decontamination system in accordance with the present invention is capable of accurately and continuously monitoring, identifying and quantifying contaminants. The system can sample the process stream continuously at one or more sampling points and route the samples to one or more analyzers to provide real time measurement of contaminant concentration. The system will log contaminant measurements and manage this data via the controller. The controller can automatically adjust the amount of decontaminant that is added to the vaporization vessel in response to detection of an elevated (or reduced) amount of contaminant in the process stream. In a described embodiment, the amount of decontaminant is adjusted by controlling the rate of fluid flow provided by the fluid pump.

In particular embodiments, the controller relays data relating to the treatment process to an operator's network system. In particular embodiments, the controller can also generate an alarm and automatically contact an "on call" technician, as needed. The operator also has the ability, via Modbus protocol, to make remote setting changes as well as turn on and off the primary pump system and any backup pump system.

In a described embodiment, components of a decontamination system are incorporated into a skid-mounted portable module that can be integrated into a process stream site. The skid-mounted components would typically include a vaporization vessel, atomizing assembly, controller, contaminant analyzer and fluid pumps. In addition, the module would include decontaminant sensors, suitable conduits and power supply.

BRIEF DESCRIPTION OF THE DRAWINGS

For detailed understanding of the invention, reference is made to the following description of the preferred embodiments. The descriptions and drawings are solely for illustrative purposes and are not limiting of possible variants.

DETAILED DESCRIPTION OF THE PREFERRED EMBODIMENTS

Figure 1:
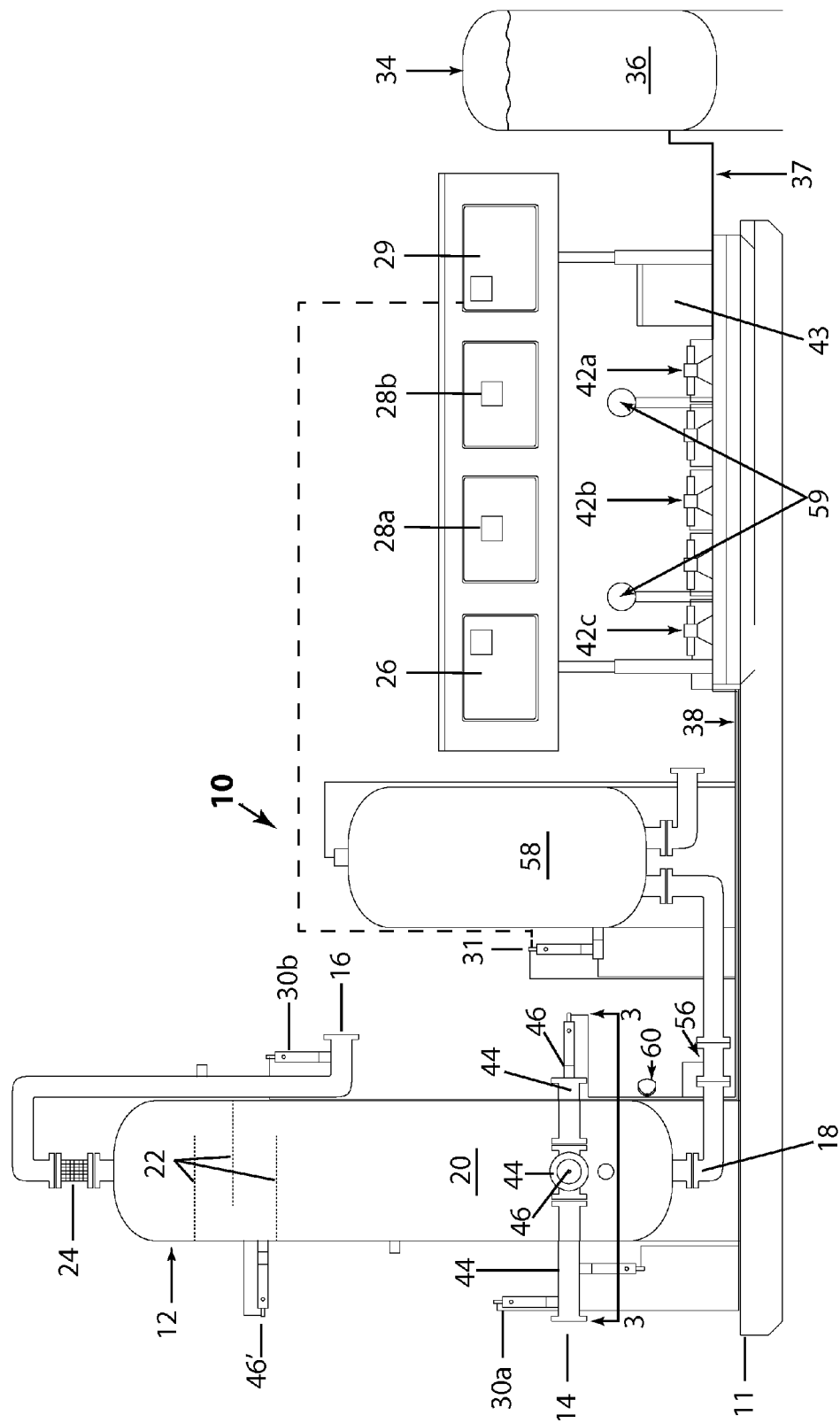
FIG. 1 is a side, partial cross-sectional view of an exemplary decontamination system in accordance with the present invention.
Figure 2:
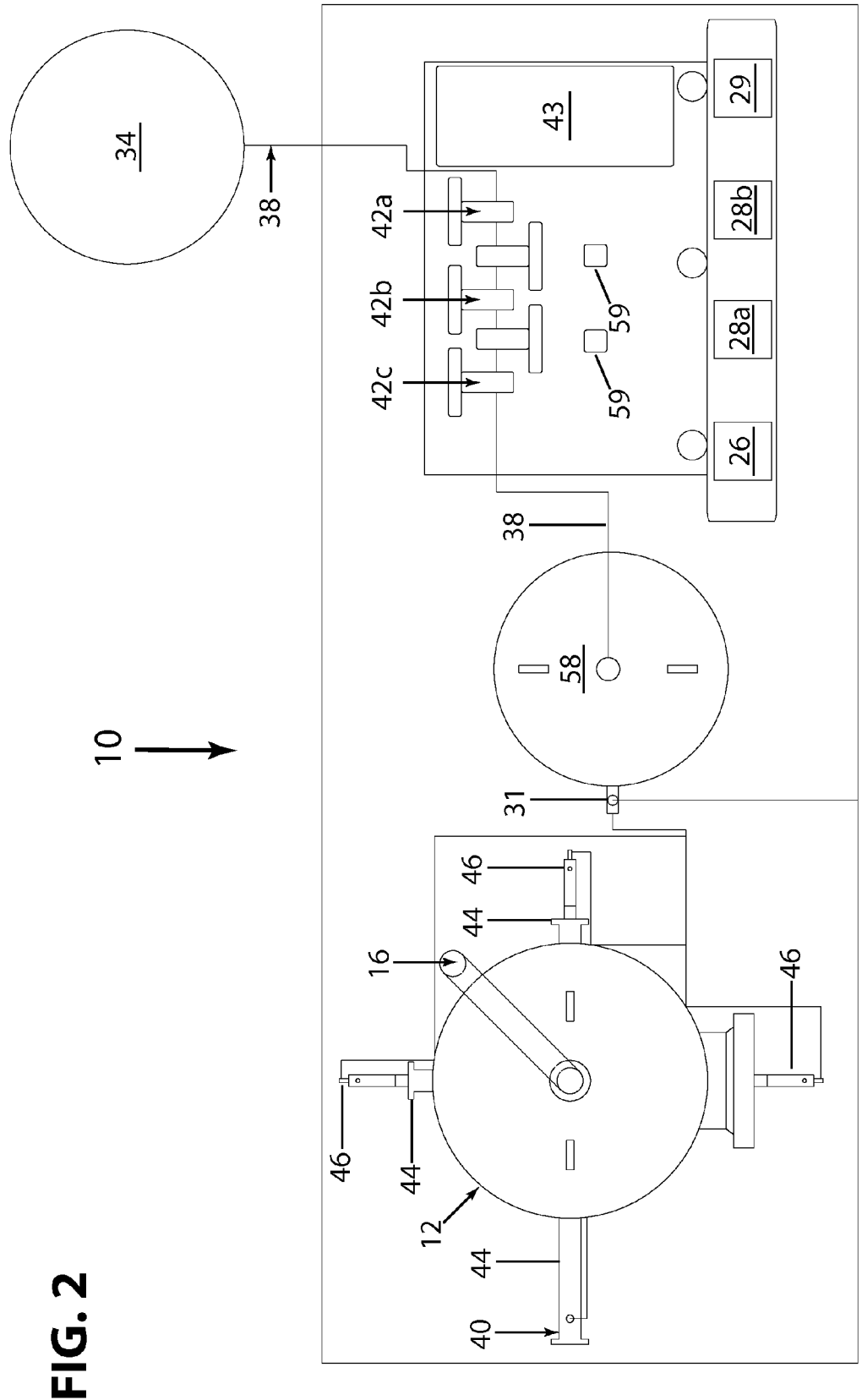
FIG. 2 is a top view of the exemplary decontamination system shown in FIG. 1.

FIGS. 1 and 2 illustrate an exemplary decontamination system 10 that is constructed in accordance with the present invention. The decontamination system 10 is operably associated with a process stream that contains at least one contaminant of interest to be neutralized. In particular embodiments, the process stream can be natural gas flowing through a pipeline. The process stream could also be a flow of other liquids, such as crude oil or water. Typical contaminants include hydrogen sulfide ($H_2S$), mercaptans, carbon dioxide ($CO_2$), oxygen ($O_2$), water ($H_2O$) and biological populations. In addition, a detected "contaminant," as discussed herein, can include conditions that can lead to contaminants, such as conditions that are ideal for hydrate formation or corrosion.

In certain embodiments, the decontamination system 10 of the present invention can be configured as a portable, modular system that is designed to be readily moved and integrated into an existing facility having a process stream that requires decontamination. Such a facility might be a pipeline that carries a flow of natural gas which it is desired to monitor. FIGS. 1 and 2 depict components of the system 10 being incorporated onto a skid or slab 11 that can be moved from place to place using cranes, low-bed trailers or other transport means known in the art. When emplaced at an existing facility, the decontamination system can be incorporated into the existing facility's process stream with the use of piping and junctions to reroute all or portions of the process stream through the system 10.

The exemplary decontamination system 10 includes a vaporization vessel 12 having a natural gas inlet 14 and natural gas outlet 16. The vessel 12 is preferably provided with a drain 18 proximate its lower end. The vaporization vessel 12 defines an interior chamber 20. Within the chamber 20, natural gas in a gaseous state rises from the inlet 14 toward the outlet 16. In a preferred embodiment, baffle plates 22 are located within the chamber 20. The baffle plates 22 will slow the gas down and promote liquid drop out. Also in a preferred embodiment, a wire mesh screen or vane pack coalescer 24 is located at the outlet of the chamber 20 so that natural gas flowing into the outlet 16 must pass through the screen 24. The screen 24 is preferably formed of stainless mesh or a vane pack coalescer and promotes further liquid drop out.

The decontamination system 10 also includes a controller 26. The controller 26 may be a computer with suitable programming for carrying out the process steps hereinafter described. The controller 26 is operably interconnected with one or more contaminant analyzers 28. In certain embodiments, the controller 26 receives feedback from particular components of the decontamination system 10 and automatically adjusts the decontamination process to achieve optimum mitigation of the selected contaminant(s). The controller 26 is typically responsible for data collection and transmission, alarm initiation and keeping the automated system 10 at peak performance.

Each contaminant analyzer 28 is interconnected with one or more sampling ports 30 which collectively constitute sensors for determining the amount of contaminant present in the process stream. The analyzers 28 are capable of detecting the level of a particular contaminant of interest in the natural gas being flowed into or out of the chamber 20. In the illustrated embodiment, there are two contaminant analyzers 28a and 28b.

In the depicted embodiment, there are two sampling ports 30. Sampling port 30a is operably associated with the natural gas inlet 14 so that the concentration or level of a selected contaminant entering the chamber 20 can be measured. Sampling port 30b is operably associated with the natural gas outlet 16 so that the concentration or level of a selected contaminant exiting the chamber 20 can be measured. In particular embodiments, the contaminant analyzer 28 is an analyzer using lead acetate technology. Suitable chemical analyzers for this application include Model 331 chemical analyzer available commercially from Envent Technologies or Models 802 or 903 chemical analyzers from Galvanic Applied Sciences. The analyzer 28a receives a sample from the sampling port 30a. The analyzer 28b receives samples from the output sampling port 30b.

Although only two analyzers 28a, 28b are illustrated, it is noted that in practice, there will likely be a multitude of such analyzers 28 and associated sampling ports 30. A sample from a single sampling port 30 might be routed to or through more than one analyzer 28, depending upon the number of contaminants requiring detection. Particular contaminants of interest and detection technologies include hydrogen sulfide ($H_2S$) via lead acetate and/or electrochemical technologies, carbon dioxide ($CO_2$) via infrared technologies, oxygen ($O_2$) via electrochemical technologies, and water ($H_2O$), and biological populations with an ultraviolet Photo-X fluorometer. A decontaminant data logger 29 is operably associated with a decontaminant sensor 31. The sensor 31 generates a signal based on the reactivity of the decontaminant in the recirculation tank 58. The signal is transmitted to the data logger 29 which is operably associated with the controller 26. When the signal reaches a preprogrammed set point, the decontaminant in recirculation tank 58 is considered unusable or spent, and is dumped/drained into a waste receptacle.

According to a preferred construction of the invention, the decontamination system 10 includes chemical injection in the form of a liquid atomizing system. The liquid atomizing system includes a supply 34 of decontaminant which is selected to remove or neutralize the particular contaminant that is being detected by the analyzer 28. As is the case with the analyzer 28 discussed above, there may in practice be multiple chemical supplies, such as supply 34. Each of the several supplies 34 would be selected to remove or neutralize a different contaminant from the process stream. A conduit, schematically shown at 38, transmits decontaminant liquid 36 within the supply 34 to atomizing assemblies 46 that are disposed within the vaporizing vessel 12. A fluid pump 42 flows the chemical 36 from the supply 34 to the atomizing assemblies 46. The system 10 may also include a back-up fluid pump 42a that can be engaged to flow decontaminant fluid in the event that the primary pump 42 fails. FIG. 2 also depicts a power source in the form of a bank of batteries 43 which provides power to the controller 26, decontaminant sensor 31, decontaminant data logger 29, sampling ports 30a, 30b and the contaminant analyzers 28a, 28b. The pumps 42a, 42b, 42c are preferably powered via 120 VAC or pneumatically with natural gas or instrument air.

Figure 3:
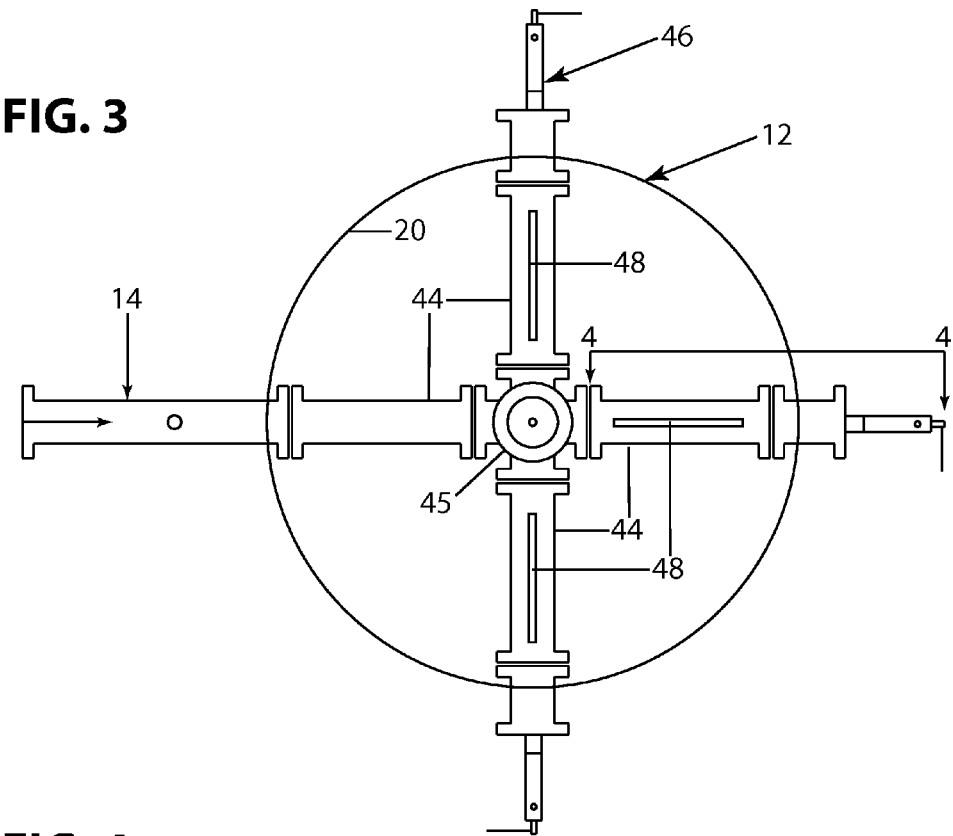
FIG. 3 is a cross-sectional view taken along lines 3-3 in FIG. 1.
Figure 4:
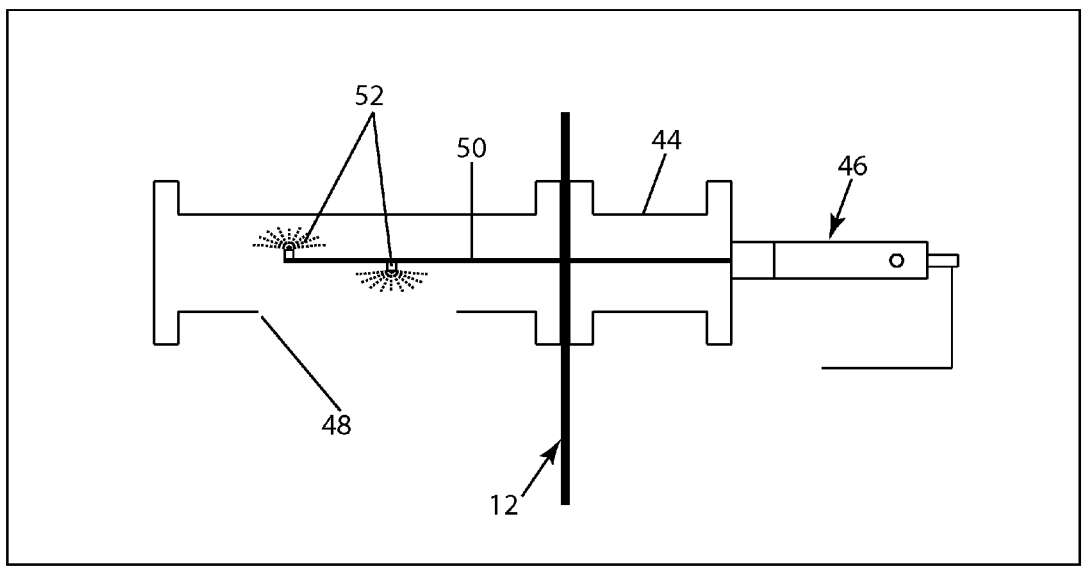
FIG. 4 is a cross-sectional view taken along lines 4-4 in FIG. 3.

The exemplary atomizing system 40, which is better seen in FIGS. 2 and 3, includes a plurality of arms 44 that project radially outwardly from a central hub 45 (see FIG. 3). In the depicted embodiment, there are four arms 44. However, there may be more or fewer than four, if desired. The arms 44 pass through the sidewall of the vaporization vessel 12. The arms 44 are preferably hollow pipes that have longitudinal slots 48 formed therein. An atomizing assembly 46 is provided for each arm 44. As best seen in FIG. 4, the atomizing assembly 46 is a rod-like member that is inserted into the end of the arm 44. Additionally, one or more additional atomizing assemblies 46 can be disposed within the chamber 20 of the vessel 12, as shown at 46' in FIG. 1. Suitable atomizing assemblies for this application include the Ready Tool Atomizer which is available commercially from Integrity Measurement & Control of Sugar Land, Tex. Shaft 50 of the atomizing assembly 46 resides radially within the arm 44 and connects to one or more nozzles 52 through which decontaminant liquid is sprayed. It is noted that the slots 48 are preferably formed within the bottom surface of each arm 44.

During operation, the process stream in gaseous state enters the interior chamber 20 of the vaporization vessel 12 through the fluid inlet 14 and flows into the arms 44 of the atomizing system 40. The pump 42 flows decontaminant liquid through conduit 38 and into each of the atomizing assemblies 46. Pumps 42 are controlled by the controller 26. The controller 26 is capable of adjusting the speed or throughput of pumps 42 so that the amount of decontaminant fluid that is provided to the atomizing assemblies 46 can be increased or decreased, as needed. The decontaminant fluid is sprayed through the nozzles 52 of the atomizing assemblies 46 within the confines of the arms 44, thereby exposing the contaminated process stream directly to the decontaminant liquid. The process stream will exit the arms 44 through the slots 48 and rise toward the fluid outlet 16 at the upper end of the chamber 20. As the process stream contacts the baffles 22 and screen 24, liquid will condense and fall to the drain 18.

Atomization physically disperses the decontaminant liquid into ultra-fine droplets or a fog. This inventor has found that this dispersion increases the contact area and time of exposure between the decontaminant and the product into which it is injected to better mitigate a contaminant present in the process stream. The fogging maximizes the surface area of the injected chemical so that contact with the contaminant is optimized and consumption of chemical is minimized. Atomization or fogging of a liquid is accomplished by forcing the liquid through a small orifice or nozzle at a very high pressure. The liquid forms ultra-fine droplets as it exits the nozzle tip. According to preferred embodiments of the present invention, the atomizing nozzles 52 produce droplets that are no larger than 50 microns in diameter. Increased fluid pressure from pump 42, provides finer droplets, and finer droplets have greater overall surface area. Also in preferred embodiments, the pump 42 provides fluid pressure that is from about 100 psi to about 3000 psi above the process pressure. In particularly preferred embodiments, the pump 42 provides fluid pressure that is from about 500 psi to about 700 psi above process pressure.

In a currently preferred embodiment, decontamination system 10 includes a recirculation mechanism that allows reuse of chemical decontaminants during operation so that the amount of decontaminant used in the system can be minimized. The recirculation mechanism includes the drain 18 and dump valve 56 which can be opened to allow liquid that has fallen into the drain 18 of the vessel 12 to be flowed into a recirculation tank 58 under the impetus of recirculation pump 42c. Accumulated chemical collects in the bottom of the vaporization vessel 12. Once a level sensor or float or switch is tripped, the chemical is dumped through drain 18 and will flow into recirculation tank 58. As a result, the recirculation tank 58 will contain some useable decontaminant as well as some spent decontaminant. With the exception of initial startup, the vaporization vessel 12 receives decontaminant chemical from the recirculation tank 58. The chemical sensor 31, in conjunction with data logger 29, monitors the chemical within the recirculation tank 58 to determine when it is completely saturated with $H_2S$ or spent such that it is not capable of further scavenging. When the controller 26 receives data indicating that the high set point for spent chemical has been reached, a dump is opened, and the spent chemical is pumped to a waste tank. Fresh chemical is pumped into the recirculation tank 58 to continue the decontamination process. One suitable device for use as the chemical sensor 31 and associated data logger 29 is a UV Photo-X Fluorometer manufactured by Custom Sensors & Technologies of Plano, Tex.

In particular embodiments, chemical meters 59 are used to measure the amount of fresh decontaminant chemical that is provided to the recirculation tank 58. Thus, the amount of fresh chemical is quantified as it is used. This allows for accurate setting of the injection rate, locally and remotely, and these rates can be compared against a tank level controller. On-line pump diagnostics, as well as a leak detection system can be provided with this combined data. The pumps 42 are set at 100% when first commissioned. As the pumps 42 wear, the discharge and tank draw down is less than when first set. An operator can adjust the pump rate to account for the wear. Also, the feedback data indicates when maintenance is required on the pumps 42.

Figure 6A:
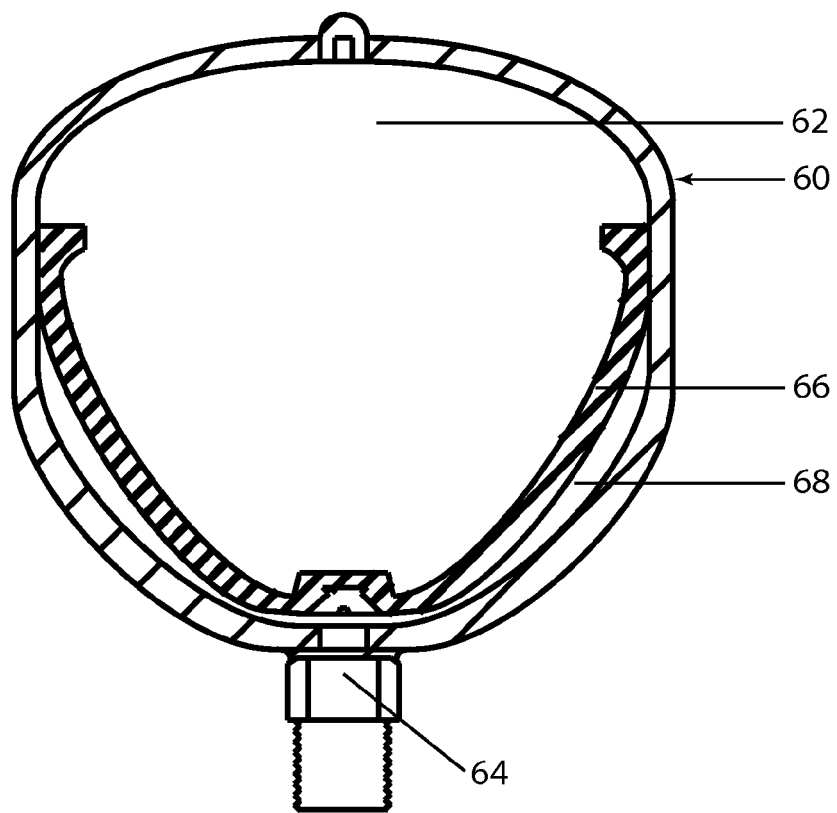
FIG. 6A is a side, cross-sectional view of an exemplary pulsation dampener that may be used with the decontamination system shown in FIGS. 1-4 and wherein the flexible bladder of the pulsation dampener is relaxed.
Figure 6B:
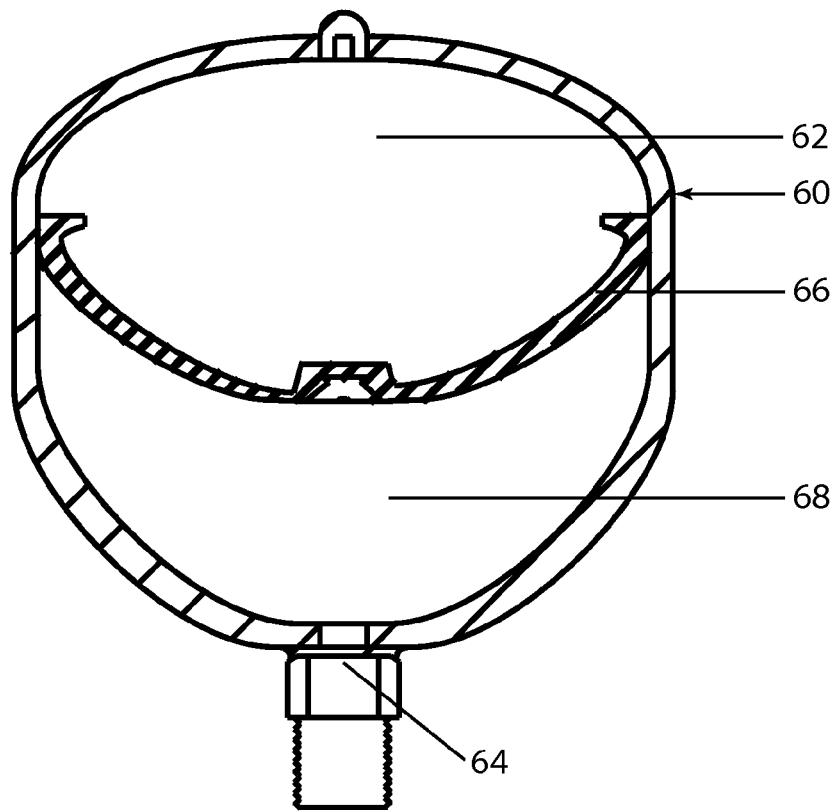
FIG. 6B is a side, cross-sectional view of the pulsation dampener of FIG. 6A wherein the flexible bladder of the pulsation dampener is compressed.

In particular embodiments, the conduit 38 of the liquid atomizing system includes a pulsation dampener 60 that is located between the pump(s) 42, 42a and the atomizing assemblies 46. The pulsation dampener 60 prevents fluid pressure spikes from causing inconsistent atomization from the individual nozzles 52. FIG. 6 is a side cross-sectional view of an exemplary pulsation dampener 60 constructed in accordance with the present invention. In a currently preferred embodiment, the pulsation dampener 60 is a pressure-loaded accumulator having an interior chamber 62 and an exterior chamber 68. The interior chamber 62 is separated from the exterior chamber 68 with a flexible bladder 66. The interior chamber 62 is preloaded with a compressible inert gas at a prescribed pressure. The exterior chamber 68 has an opening 64 that leads to the conduit 38 containing decontaminant chemical. The relaxed bladder 66 is compressed until the inert gas precharge can no longer compress. During the backstroke cycle of the pumps 42, when there is no pressure being provided to the atomizing assembly 46, the pulsation dampener bladder 66 will become a secondary pump as the bladder 66 applies pressure to the liquid stream, thus maintaining pressure useful for fine atomization.

Figure 5:
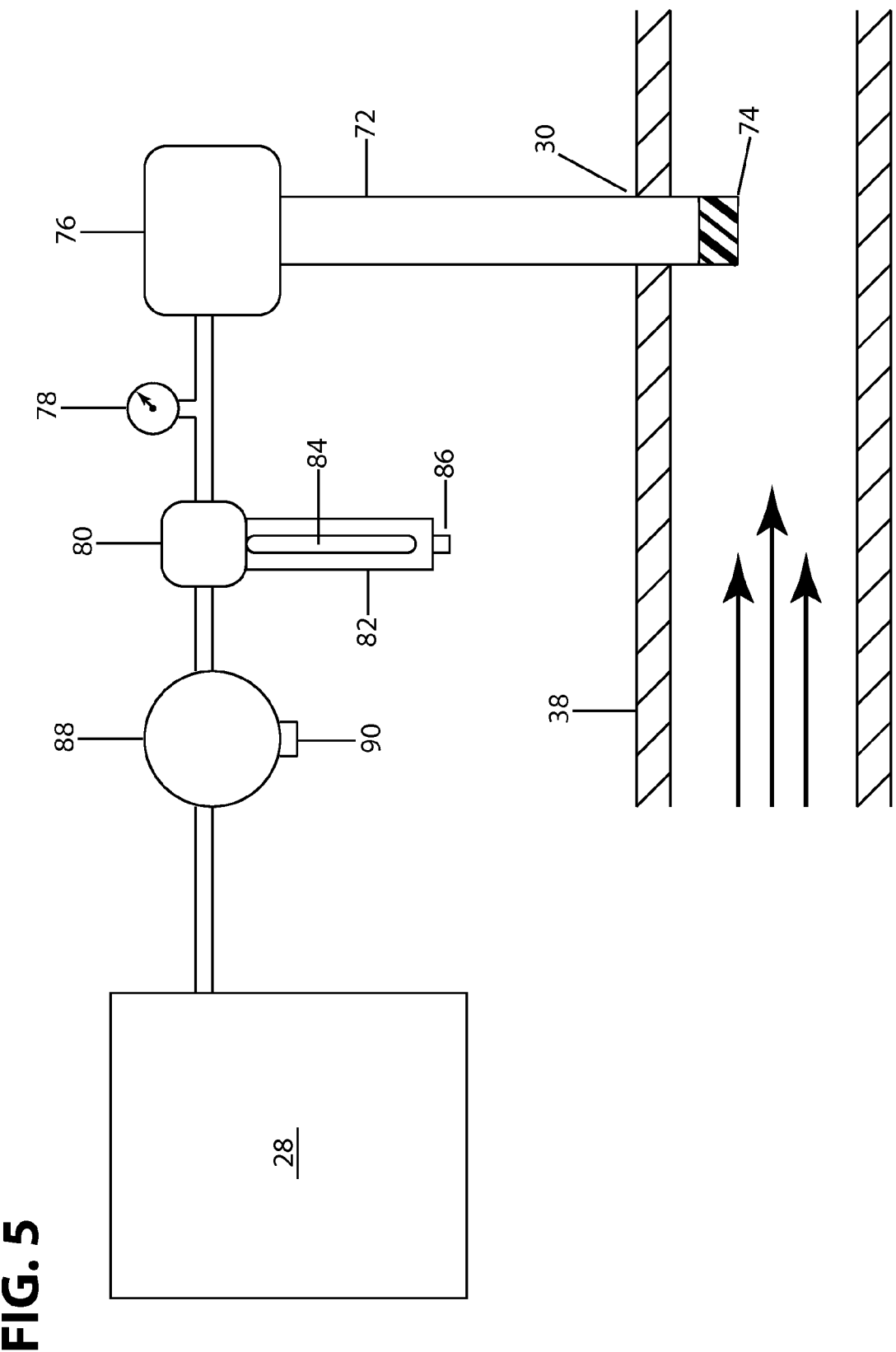
FIG. 5 is an exemplary conditioning pathway that is useful in conjunction with the decontamination system shown in FIGS. 1-4 for transmission of a process stream sample from a sampling port to a chemical/contaminant analyzer.

FIG. 5 illustrates an exemplary sample pathway that can be used to transmit a sample of the process stream from a sampling port 30 to an analyzer 28. The sample pathway conditions the sample that is being transmitted so as to substantially remove liquid that might contain decontaminant from the sample and which might lead to an inaccurate reading by the analyzer 28. The pathway includes a probe 72 that is affixed to the port 30 (a or b) and placed into contact with the process stream in conduit 38. The lower end of the probe 72 includes a porous disc 74 which may be made of TEFLON® or a similar material and which is suitable for screening or filtering small solids or liquid from a gaseous sample of the process stream. The probe 72 transmits the sample to a pressure regulator 76 of a type known in the art which adjusts the pressure of the sample so that it can be handled by the analyzer 28. Pressure gauge 78 provides a visual indicator of the adjusted pressure of the sample as it is transmitted from the pressure regulator 76 to a coalescing filter 80. The coalescing filter 80 includes an outer housing 82 that encloses a cylindrical filter element 84. A drain valve 86 is located proximate the bottom of the housing 82. Process stream entering the coalescing filter 80 will pass through the filter element 84 which will remove liquids from the process stream, including coalesced decontaminant chemical. Removed liquids can be dispensed from coalescing filter 80 via the drain valve 86. The process stream sample will exit the coalescing filter 80 and enter membrane filter 88. Membrane filter 88 will remove any remaining liquid, including liquid decontaminant chemical from the process stream sample before the sample enters the analyzer 28. A drain valve 90 located proximate the lower end of the membrane filter 88 to allow removed water and decontaminant chemical to be dispensed from the membrane filter 88. Removal of water and decontaminant from the process stream sample before the sample enters the analyzer 28 is referred to herein as conditioning the sample.

The invention provides methods for decontaminating at least one contaminant in a process stream. According to an exemplary method of operation, a process stream is flowed into the vaporization vessel 12 in a gaseous state. Decontaminant liquid is dispersed within the chamber 20 of the vessel using atomization assemblies 46. During this process, the controller 26 obtains data from the contaminant analyzers 28a and 28b. The level of contamination that is detected by input analyzer 28a is used by an operator to scale down the field injection feeding into the vaporization vessel 12, further saving chemical waste and money. The outlet analyzer 28b measures for contaminant exiting the chamber 20 and compares the detected level of contaminant in the process stream leaving the chamber 20 to a predetermined level or setpoint. Typically, all such measurements are sent to the controller 26 24 hours a day, 7 days a week. The controller 26 then adjusts the pumps 42 to increase or decrease the flow of decontaminant liquid in response to the analysis. When decontaminated, the process stream is ready to enter the transmission grid.

The effectiveness of chemical treatment for a given contaminant depends upon both the dynamics of the process into which the chemical is injected and the dynamics of the injection system. In particular aspects, the systems and methods of the present invention overcome challenges to effective treatment of contaminants through the use of an in-line vaporization vessel 12. This approach effectively incorporates decontaminants while avoiding the changes in flow patterns that can occur at elbows, valves and other obstructions within a pipeline. The vaporization vessel 12 removes both coalesced and spent decontaminants.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A system for decontaminating a hydrocarbon process stream containing at least one contaminant, the system comprising:
   a supply of decontaminant fluid;
   a controller associated with the supply of decontaminant fluid and operable to introduce a controlled amount of decontaminant to the hydrocarbon process stream;
   one or more atomizing nozzles to disperse decontaminant fluid as an atomized fog into the hydrocarbon process stream; and
   a chemical sensor to monitor dispersed decontaminant fluid to determine the extent of reactivity of the dispersed decontaminant fluid relative to fresh decontaminant fluid.

2. The system of claim 1 further comprising:
   a vaporization vessel into which the hydrocarbon process stream is flowed in a gaseous state, the vaporization vessel having a fluid inlet, through which the hydrocarbon process stream enters the vaporization vessel, and a fluid outlet, through which the hydrocarbon process stream exits the vaporization vessel; and wherein the one or more atomizing nozzles disperse decontaminant fluid into the hydrocarbon process stream within the vaporization vessel.

3. The system of claim 2 further comprising:

a first contaminant analyzer operably associated with the fluid outlet to measure an amount of the at least one contaminant within the hydrocarbon process stream exiting the vaporization vessel; and the first contaminant analyzer providing information relating to the measured amount of the at least one contaminant to the controller.

4. The system of claim 1 wherein the one or more atomizing nozzles disperses the decontaminant liquid into a fog having droplets no larger than 50 microns in diameter.

5. The system of claim 1 further comprising a fluid pump operably associated with the supply of decontaminant fluid and being adjustable by the controller to adjust the amount of decontaminant fluid that is introduced to the hydrocarbon process stream.

6. The system of claim 1 wherein the hydrocarbon process stream comprises natural gas.

7. The system of claim 1 wherein the at least one contaminant comprises hydrogen sulfide.

8. A system for decontaminating a hydrocarbon process stream containing at least one contaminant, the system comprising:

a supply of decontaminant fluid;

a controller associated with the supply of decontaminant fluid and operable to introduce a controlled amount of decontaminant to the hydrocarbon process stream; and one or more atomizing nozzles to disperse decontaminant fluid as an atomized fog into the hydrocarbon process stream, and wherein the fog has droplets no larger than 50 microns in diameter;

a chemical sensor to monitor dispersed decontaminant fluid to determine the extent of reactivity of the dispersed decontaminant fluid, the chemical sensor providing a signal to the controller to allow the controller to determine the reactivity of the dispersed decontaminant fluid relative to fresh decontaminant fluid; and the controller opening a dump valve to eliminate dispersed decontaminant fluid when it determines that the dispersed decontaminant fluid is not capable of sufficient reactivity.

9. The system of claim 8 further comprising:

a vaporization vessel into which the hydrocarbon process stream is flowed in a gaseous state, the vaporization vessel having a fluid inlet, through which the hydrocarbon process stream enters the vaporization vessel, and a fluid outlet, through which the hydrocarbon process stream exits the vaporization vessel; and wherein the one or more atomizing nozzles disperse decontaminant fluid into the hydrocarbon process stream within the vaporization vessel.

10. The system of claim 9 further comprising:

a first contaminant analyzer operably associated with the fluid outlet to measure an amount of the at least one contaminant within the hydrocarbon process stream exiting the vaporization vessel; and the first contaminant analyzer providing information relating to the measured amount of the at least one contaminant to the controller.

11. The system of claim 9 further comprising:

a second contaminant analyzer operably associated with the fluid inlet to measure an amount of the at least one contaminant within the hydrocarbon process stream entering the vaporization vessel; and the second contaminant analyzer providing information relating to the measured amount of the at least one contaminant to the controller.

12. The system of claim 8 further comprising a fluid pump operably associated with the supply of decontaminant fluid and being adjustable by the controller to adjust the amount of decontaminant fluid that is introduced to the hydrocarbon process stream.

13. The system of claim 8 wherein the hydrocarbon process stream comprises natural gas.

14. The system of claim 8 wherein the at least one contaminant comprises hydrogen sulfide.

15. The system of claim 8 wherein the atomized fog brings greater surface area of the injected decontaminant fluid into contact with the hydrocarbon production stream to reduce consumption of injected decontaminant fluid.

16. A method for decontaminating at least one contaminant in a hydrocarbon process stream, the method comprising the steps of:

atomizing a decontaminant fluid into a fog;

dispersing a controlled amount of the atomized decontaminant fluid into the hydrocarbon process stream;

determining reactivity of dispersed decontaminant fluid;

comparing the reactivity of dispersed decontaminant fluid to reactivity of fresh decontaminant fluid.

17. The method of claim 16 further comprising the step of flowing the hydrocarbon process stream into a vaporization vessel in a gaseous state.

18. The method of claim 17 wherein the vaporization vessel promotes decontamination and reduced decontaminant usage.

19. The method of claim 16 further comprising the steps of:

dumping spent decontamination fluid if the reactivity of dispersed decontaminant fluid is insufficient; and recirculating spent decontamination fluid if the reactivity of dispersed decontaminant fluid is sufficient.

* * * * *